(12) United States Patent
Hummert et al.

(10) Patent No.: US 10,128,442 B2
(45) Date of Patent: Nov. 13, 2018

(54) SUBSTITUTED 1,2,3-TRIYLIDENETRIS (CYANOMETHANYLYLIDENE) CYCLOPROPANES FOR VTE, ELECTRONIC DEVICES AND SEMICONDUCTING MATERIALS USING THEM

(71) Applicant: Novaled GmbH, Dresden (DE)

(72) Inventors: Markus Hummert, Dresden (DE); Achim Bruch, Dresden (DE); Christiane Köhn, Dresden (DE); Max P. Nüllen, Dresden (DE); Ulrich Heggemann, Dresden (DE)

(73) Assignee: Novaled GmbH, Dresden (DE)

( * ) Notice: Subject to any disclaimer, the term of this patent is extended or adjusted under 35 U.S.C. 154(b) by 0 days.

(21) Appl. No.: 15/536,778

(22) PCT Filed: Dec. 16, 2015

(86) PCT No.: PCT/EP2015/080046
§ 371 (c)(1),
(2) Date: Jun. 16, 2017

(87) PCT Pub. No.: WO2016/097017
PCT Pub. Date: Jun. 23, 2016

(65) Prior Publication Data
US 2017/0373251 A1    Dec. 28, 2017

(30) Foreign Application Priority Data
Dec. 16, 2014   (EP) .................................... 14198165

(51) Int. Cl.
*H01L 29/08*   (2006.01)
*H01L 35/24*   (2006.01)
(Continued)

(52) U.S. Cl.
CPC .......... *H01L 51/005* (2013.01); *C07C 255/51* (2013.01); *C07D 213/84* (2013.01);
(Continued)

(58) Field of Classification Search
CPC . H01L 51/005; H01L 51/0067; H01L 51/001; C07D 213/84; C07D 239/30; C09K 11/06; C07C 255/51
See application file for complete search history.

(56) References Cited

U.S. PATENT DOCUMENTS

2010/0288362 A1   11/2010   Hatwar et al.
2012/0223926 A1   9/2012    Morii et al.

FOREIGN PATENT DOCUMENTS

EP     2684932 A1    1/2014

OTHER PUBLICATIONS

PCT International Search Report and Written Opinion for PCT Application No. PCT/EP2015/080046 dated Mar. 17, 2016 (11 pages).
(Continued)

*Primary Examiner* — William F Kraig
*Assistant Examiner* — Vicki B Booker
(74) *Attorney, Agent, or Firm* — Eversheds Sutherland (US) LLP

(57) ABSTRACT

Provided are processes for preparing an electrically doped semiconducting material that includes a [3]-radialene p-dopant. Also provided are processes for preparing an electronic device containing a layer that includes a [3]-radialene p-dopant. The processes may include (i) loading an evaporation source with a [3]-radialene p-dopant and (ii) evaporating the [3]-radialene p-dopant at an elevated temperature and at a reduced pressure. The [3]-radialene p-dopant may be selected from compounds having a structure according to formula (I) herein.

19 Claims, 1 Drawing Sheet

(51) Int. Cl.
- *H01L 51/00* (2006.01)
- *C07D 213/84* (2006.01)
- *C09K 11/06* (2006.01)
- *C07C 255/51* (2006.01)
- *C07D 239/30* (2006.01)
- *H01L 51/50* (2006.01)

(52) U.S. Cl.
CPC ............ *C07D 239/30* (2013.01); *C09K 11/06* (2013.01); *H01L 51/001* (2013.01); *H01L 51/0067* (2013.01); *C07C 2601/02* (2017.05); *C07C 2601/16* (2017.05); *C09K 2211/1007* (2013.01); *C09K 2211/1018* (2013.01); *H01L 51/506* (2013.01); *H01L 51/5088* (2013.01); *H01L 2251/554* (2013.01)

(56) References Cited

OTHER PUBLICATIONS

European Search Report for EP Application No. 14198165.4 dated Jun. 3, 2015 (6 pages).
European Office Action for EP Application No. 14 198 165.4 dated Jun. 13, 2017 (6 pages).

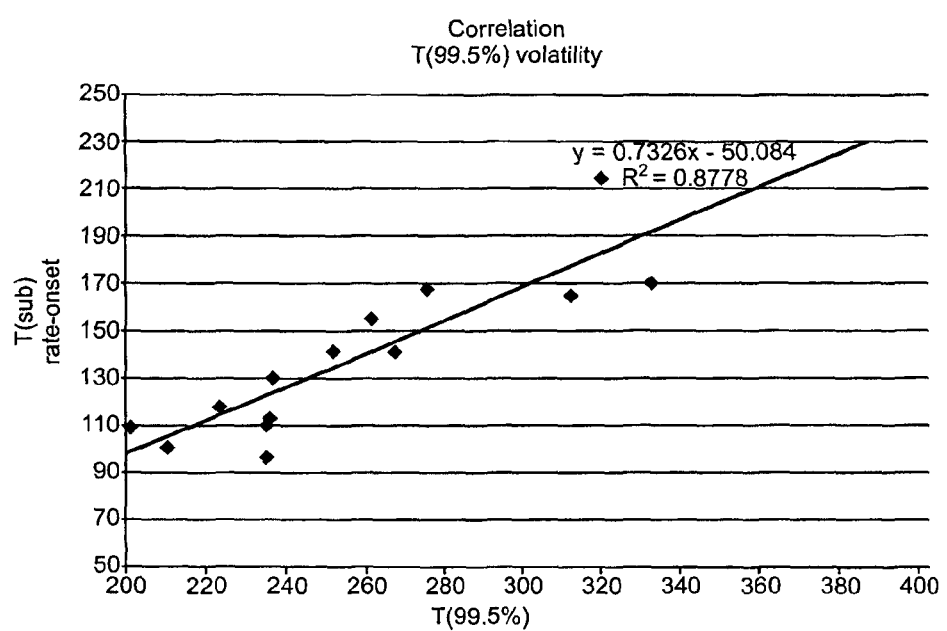

SUBSTITUTED 1,2,3-TRIYLIDENETRIS(CYANOMETHANYLYLIDENE) CYCLOPROPANES FOR VTE, ELECTRONIC DEVICES AND SEMICONDUCTING MATERIALS USING THEM

CROSS REFERENCE TO RELATED APPLICATIONS

This application is a U.S. national stage application of PCT/EP2015/080046, filed Dec. 16, 2015, which claims priority to European Application No. 14198165.4, filed Dec. 16, 2014. The contents of these applications are hereby incorporated by reference.

The present invention relates to 1,2,3-triylidenetris(cyanomethanylylidene)) cyclopropane substituted with aryl or heteroaryl groups, its use as p-dopant or hole injecting material in semiconducting electronic devices and to robust vacuum thermal evaporation (VTE) processes for manufacturing such devices.

[3]-radialene compounds with cyanomethylidene groups substituted with electron withdrawing aryls or heteroaryls have been found to be specifically useful as p-dopants for common organic light emitting diode (OLED) hole transport materials (HTMs), see e.g. U.S. Pat. No. 8,057,712 B2, herein incorporated as a reference. For an industrial production of electronic devices and semiconducting materials utilizing these compounds, mostly vacuum thermal evaporation (VTE) processes are used. In the state-of-the-art evaporation sources and at pressures below $10^{-4}$ Pa used in them, presently used materials vaporize mostly at temperatures between 150 and 300° C. For the sake of effectivity, it is preferred that the evaporation source loaded once with the material works as long as possible. Contemporary hole transport matrix compounds used in OLEDs frequently sustain their exposition to their evaporation temperatures for one or two weeks without experiencing a significant change in their impurity profile. In mass production of organic electronic devices comprising electrical dopants, an insufficient long-term thermal stability of the state-of-the-art dopants does very often represent a key limitation for the duration of a production campaign.

It is therefore an object of the present invention to provide an improved process for manufacturing electronic devices comprising radialene p-dopants and improved semiconducting materials, layers and/or electronic devices preparable by the improved process. Another object of the invention is providing improved radialene p-dopants for the improved process. Still another object of the invention is providing an improved process for preparation of the improved radialene p-dopants.

SUMMARY OF THE INVENTION

The first object is achieved by a process for preparation of an electrically doped semiconducting material comprising a [3]-radialene p-dopant or for preparation of an electronic device containing a layer comprising a [3]-radialene p-dopant, the process comprising the steps
(i) loading an evaporation source with the [3]-radialene p-dopant and
(ii) evaporating the [3]-radialene p-dopant at an elevated temperature and at a reduced pressure,
wherein the [3]-radialene p-dopant is selected from compounds having a structure according to formula (I)

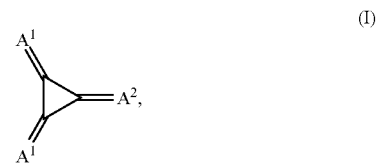

wherein $A^1$ and $A^2$ are independently aryl- or heteroaryl-substituted cyanomethylidene groups, the aryl and/or heteroaryl is selected independently in $A^1$ and $A^2$ from 4-cyano-2,3,5,6-tetrafluorphenyl; 2,3,5,6-tetrafluorpyridine-4-yl; 4-trifluormethyl-2,3,5,6-tetrafluorphenyl; 2,4-bis(trifluormethyl)-3,5,6-trifluorphenyl; 2,5-bis(trifluormethyl)-3,4,6-trifluorphenyl; 2,4,6-tris(trifluormethyl)-1,3-diazine-5-yl; 3,4-dicyano-2,5,6-trifluorphenyl; 2-cyano-3,5,6-trifluorpyridine-4-yl; 2-trifluormethyl-3,5,6-trifluorpyridine-4-yl; 2,5,6-trifluor-1,3-diazine-4-yl and 3-trifluormethyl-4-cyano-2,5,6-trifluorphenyl, and at least one aryl or heteroaryl is 2,3,5,6-tetrafluolpyridine-4-yl; 2,4-bis(trifluormethyl)-3,5,6-trifluorphenyl; 2,5-bis(trifluormethyl)-3,4,6-trifluorphenyl; 2,4,6-tris(trifluormethyl)-1,3-diazine-5-yl; 3,4-dicyano-2,5,6-trifluorphenyl; 2-cyano-3,5,6-trifluorpyridine-4-yl; 2-trifluormethyl-3,5,6-trifluorpyridine-4-yl; 2,5,6-trifluor-1,3-diazine-4-yl or 3-trifluormethyl-4-cyano-2,5,6-trifluorphenyl, provided that the heteroaryl in both $A^1$ and $A^2$ cannot be 2,3,5,6-tetrafluorpyridine-4-yl at the same time.

The vaporized compound (I) is, subsequently, either deposited in form of a neat layer, or co-deposited with an appropriate matrix material. Neat layers of compound (I) are advantageously used as hole injection or charge generation layers, which are preferably adjacent to a layer comprising the matrix material. The matrix material is preferably a hole transport matrix material comprising at least one hole transport matrix compound. Examples of hole transport matrix compounds which can be electrically doped with radialene p-dopants are well-known from earlier Novaled applications, including the applications cited herein.

Preferably, the evaporation temperature in step (ii) is in the range of 100-300° C., more preferably in the range of 125-275° C., even more preferably in the range of 150-250° C.

The pressure in step (ii) is preferably less than $10^{-1}$ Pa, more preferably less than less than $10^{-2}$ Pa, even more preferably less than $10^{-3}$ Pa, most preferably less than $10^{-4}$ Pa.

Duration of the evaporation step (ii) is, preferably, longer than 100 hours, more preferably longer than 150 hours, even more preferably longer than 200 hours.

To achieve the sufficient doping strength, the redox potential of the [3]-radialene p-dopant, measured by cyclic voltammetry (CV) in acetonitrile (ACN) against redox couple ferrocene/ferricenium (Fc/Fc) as standard, is preferably in the range from +0.10 V to +0.50 V, more preferably in the range from 0.20 to +0.40 V, even more preferably in the range from +0.25 to 0.35 V.

The first object is further achieved by the use of [3]-radialene compound selected from compounds having a structure according to formula (I)

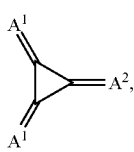

wherein A¹ and A² are independently aryl- or heteroaryl-substituted cyanomethylidene groups,
the aryl and/or heteroaryl is selected independently in A¹ and A² from 4-cyano-2,3,5,6-tetrafluorphenyl; 2,3,5,6-tetrafluorpyridine-4-yl; 4-trifluormethyl-2,3,5,6-tetrafluorphenyl; 2,4-bis(trifluormethyl)-3,5,6-trifluorphenyl; 2,5-bis(trifluormethyl)-3,4,6-trifluorphenyl; 2,4,6-tris(trifluormethyl)-1,3-diazine-5-yl; 3,4-dicyano-2,5,6-trifluorphenyl; 2-cyano-3,5,6-trifluorpyridine-4-yl; 2-trifluormethyl-3,5,6-trifluorpyridine-4-yl; 2,5,6-trifluor-1,3-diazine-4-yl and 3-trifluormethyl-4-cyano-2,5,6-trifluorphenyl, and at least one aryl or heteroaryl is 2,3,5,6-tetrafluorpyridine-4-yl; 2,4-bis(trifluormethyl)-3,5,6-trifluorphenyl; 2,5-bis(trifluormethyl)-3,4,6-trifluorphenyl; 2,4,6-tris(trifluormethyl)-1,3-diazine-5-yl; 3,4-dicyano-2,5,6-trifluorphenyl; 2-cyano-3,5,6-trifluorpyridine-4-yl; 2-trifluormethyl-3,5,6-trifluorpyridine-4-yl; 2,5,6-trifluor-1,3-diazine-4-yl or 3-trifluormethyl-4-cyano-2,5,6-trifluorphenyl, provided that the heteroaryl in both A¹ and A² cannot be 2,3,5,6-tetrafluorpyridine-4-yl at the same time,
as a p-dopant or hole injection material in electronic devices.

The first object is further achieved by a semiconducting material, semiconducting layer and/or electronic device comprising the radialene compound having formula (I), wherein the experimental OLED built on a glass substrate provided with an ITO anode, 10 nm thick hole injection transport layer (HIL) consisting of commercially available biphenyl-4-yl(9,9-diphenyl-9H-fluoren-2-yl)-[4-9-phenyl-9H-carbazol-3-yl)phenyl]-amine (CAS number 1242056-42-3) doped with 8 weight % of the tested compound, 130 nm thick hole transport layer made of the same matrix compound as the HIL, 20 nm thick emitting layer made of commercially available host compound ABH113 with 3 wt % emitter NUBD370 (both from the same supplier Sun Fine Chemicals, Korea), 36 nm thick electron transport layer made of (3-(dibenzo[c,h]acridin-7-yl)phenyl)diphenylphosphine oxide and lithium 8-hydroxyquinolinolate (LiQ, 1:1 w/w), and 30 nm thick silver cathode, as described in the device example below, may be excluded, as well as may be excluded the doped material consisting of biphenyl-4-yl(9,9-diphenyl-9H-fluoren-2-yl)-[4-9-phenyl-9H-carbazol-3-yl)phenyl]-amine doped with 8 weight % of any compound selected from compounds A1, A2, A3, A4, A5, A6, A7, A8 and compounds B1, B2, B3, B4, B5, B6, B7 as listed below and/or the 10 nm thick layer of such doped material.

Preferably, the semiconducting material or semiconducting layer comprising the compound having formula (I) is comprised between a first electrode and a second electrode. Also preferably, the first electrode is anode and the second electrode is cathode. In one of preferred embodiments, the layer comprising the compound of formula (I) is adjacent to the anode. In another preferred embodiment, the layer comprising the compound of formula (I) serves as a charge generating layer. Also preferably, the electronic device is an OLED, in one of preferred embodiments, a tandem OLED.

The second object is achieved by a [3]-radialene compound having a structure according to formula (I)

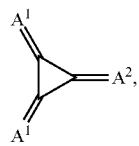

wherein
A¹ and A² are independently aryl- or heteroaryl-substituted cyanomethylidene groups,
the aryl and/or heteroaryl is selected independently in A¹ and A² from 4-cyano-2,3,5,6-tetrafluorphenyl; 2,3,5,6-tetrafluorpyridine-4-yl; 4-trifluormethyl-2,3,5,6-tetrafluorphenyl; 2,4-bis(trifluormethyl)-3,5,6-trifluorphenyl; 2,5-bis(trifluormethyl)-3,4,6-trifluorphenyl; 2,4,6-tris(trifluormethyl)-1,3-diazine-5-yl; 3,4-dicyano-2,5,6-trifluorphenyl; 2-cyano-3,5,6-trifluorpyridine-4-yl; 2-trifluormethyl-3,5,6-trifluorpyridine-4-yl; 2,5,6-trifluor-1,3-diazine-4-yl and 3-trifluormethyl-4-cyano-2,5,6-trifluorphenyl,
and at least one aryl or heteroaryl is 2,3,5,6-tetrafluorpyridine-4-yl; 2,4-bis(trifluormethyl)-3,5,6-trifluorphenyl; 2,5-bis(trifluormethyl)-3,4,6-trifluorphenyl; 2,4,6-tris(trifluormethyl)-1,3-diazine-5-yl; 3,4-dicyano-2,5,6-trifluorphenyl; 2-cyano-3,5,6-trifluorpyridine-4-yl; 2-trifluormethyl-3,5,6-trifluorpyridine-4-yl; 2,5,6-trifluor-1,3-diazine-4-yl or 3-trifluormethyl-4-cyano-2,5,6-trifluorphenyl, provided that the heteroaryl in both A¹ and A² cannot be 2,3,5,6-tetrafluorpyridine-4-yl at the same time.

The inventive design of compound (I) enables that in embodiments of the inventive process, wherein the compound (I) is co-evaporated and subsequently co-deposited with a hole transport matrix material, for any hole transport matrix compound having the vaporization temperature in the range 100-300° C. and redox potential in the range 0.00-0.50 V vs Fc⁺/Fc reference redox pair in acetonitrile, a thermally robust compound (I) with sufficient p-doping strength and with vaporization temperature differing less than 50° C. from the vaporization temperature of the chosen hole transport matrix compound can be selected.

The third object is achieved by process for synthesis of a [3]-radialene compound having a structure according to formula (I)

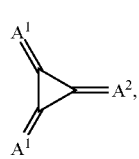

wherein
A¹ and A² are independently aryl- or heteroaryl-substituted cyanomethylidene groups,
the aryl and/or heteroaryl is selected independently in A¹ and A² from 4-cyano-2,3,5,6-tetrafluorphenyl; 2,3,5,6-tetrafluorpyridine-4-yl; 4-trifluormethyl-2,3,5,6-tetrafluorphenyl; 2,4-bis(trifluormethyl)-3,5,6-trifluorphenyl; 2,5-bis(trifluormethyl)-3,4,6-trifluorphenyl; 2,4,6-tris(trifluormethyl)-1,3-diazine-5-yl; 3,4-dicyano-2,5,6-trifluorphenyl; 2-cyano-3,5,6-trifluorpyridine-4-yl; 2-trifluormethyl-3,5,6-trifluorpyridine-4-yl; 2,5,6-trifluor-1,3-diazine-4-yl and 3-trifluormethyl-4-cyano-2,5,6-trifluorphenyl, and at least one aryl or heteroaryl is 2,3,5,6-tetrafluorpyridine-4-yl; 2,4-bis(trifluormethyl)-3,5,6-trifluorphenyl; 2,5-bis(trifluormethyl)-3,4,6-trifluorphenyl; 2,4,6-tris(trifluormethyl)-1,3-diazine-5-yl; 3,4-dicyano-2,5,6-trifluorphenyl; 2-cyano-3,5,6-trifluorpyridine-4-yl; 2-trifluormethyl-3,5,6-trifluorpyridine-4-yl; 2,5,6-trifluor-1,3-diazine-4-yl or 3-trifluormethyl-4-cyano-2,5,6-trifluorphenyl, provided that the heteroaryl in both $A^1$ and $A^2$ cannot be 2,3,5,6-tetrafluorpyridine-4-yl at the same time,
wherein the last synthesis step, in which the compound of formula (I) is formed, is carried out in a solvent comprising at least one saturated halogenated carboxylic acid. It is to be understood that the saturated carboxylic acid does comprise only single (sigma) carbon-carbon bonds. The saturated halogenated carboxylic acid may be aliphatic or alicyclic. More preferred is the saturated halogenated carboxylic acid which is liquid at 20° C., even more preferred is the saturated halogenated carboxylic acid which is liquid at 0° C. In one embodiment, the saturated halogenated carboxylic acid is a saturated perhalogenated carboxylic acid. In a preferred embodiment, the saturated perhalogenated carboxylic acid is trifluoroacetic acid.

Preferably, the concentration of the saturated halogenated carboxylic acid is in the range 5-95 wt %, more preferably in the range 10-90 wt %, even more preferably in the range 15-85 wt %, most preferably in the range 20-80 wt %.

The solvent may further comprise a saturated carboxylic acid and/or an inorganic acid. The saturated carboxylic acid may be acetic acid, the inorganic acid may be nitric acid.

Preferably, an oxidant is present in the last synthesis step, wherein compound (I) is formed. Also preferably, nitric acid serves also as the oxidant. Also preferably, nitric acid comprises water. Also preferably, the last synthesis step, wherein compound (I) is formed, is substantially free of a free halogen, as described in WO2015/007729. Also preferably, the reaction temperature in the last synthesis step is in the range 0-100° C., more preferably in the range 10-90° C., even more preferably in the range 15-85° C., most preferably in the range 20-80° C. Particularly high yield and/or purity is achieved when using this process.

BRIEF DESCRIPTION OF DRAWINGS

FIG. 1 shows the correlation between the temperature $T_{99.5}$ of 0.5% weight loss in TGA analysis at normal pressure and the rate onset temperature measured in high vacuum test chamber $T_{rc}$ (in the graphassigned as $T_{sub}$); the correlation expressed as linear relationship $y=0.7326*T_{99.5\%}-50.084$ was used for the estimation of the values $T_{rc}$ for the compounds, wherein the experimental value was not yet available.

DETAILED DESCRIPTION OF THE INVENTION

[3]-radialene p-dopants known from U.S. Pat. No. 8,057,712 B2 were proven as a very successful p-doping concept, especially for OLED displays, as may be taken from further documents like WO2010/075836, WO2010/132236, WO2011/134458, WO2014/009310, US2012/223296, WO2013/135237, WO2014/037512, WO2014/060526.

Depending on the device design and specific compounds chosen as matrices for hole transporting, electron blocking and and/or emitting layers in which or adjacent to the p-dopants might be used, the energy level of the lowest unoccupied molecular orbital (LUMO) of the dopant as well as its optimum evaporation temperature required for the optimum fit with the chosen hole transport matrix and with properties of materials chosen for adjacent layers may vary in a quite broad range.

This variability was the primary incentive for further development of new compounds with the goal to offer a broad spectrum of [3]-radialene p-dopants, enabling to offer for each particular case a dopant fitting well to highest occupied molecular orbital (HOMO) energy level of the chosen matrix as well as to evaporation temperature of this matrix in industrial evaporation sources.

The common denominator for selection of applicable structures was the requirement of high long-term thermal stability of the offered p-dopant, allowing reasonably long production campaign with the evaporation source loaded with the compound.

In candidate compounds, the fulfillment of this requirement has been checked by especially designed "ampulla tests". Samples of each particular compound divided into quartz ampoules and sealed under vacuum were kept in a thermostat at various temperatures for times in the range 100-350 hours. Changes in sample impurity profile were checked by spectroscopic and chromatographic methods specifically designed for [3]-radialene p-dopants. Finally, specific structural motives enabling stable purity for at least 100 hour processing time at evaporation temperature of the compound were identified.

The new structural motives consist in new substitution patterns of the aryl or heteroaryl substituent in the formula (I). Further research showed that by combining newly identified advantageous structural features in one radialene molecule together or combining them with selected substitution patterns already known from the previous art allows for the desired broad series of thermally robust p-dopants with various strength and volatility.

With regard to formula (I), all $A^1$'s are equal, but $A^1$ and $A^2$ can be the same or different from each other.

It should be understood that for the sake of brevity, all compounds of formula (I) having substitution pattern in structural moieties $A^1$ and $A^2$ equal are in this application assigned as "symmetric". Similarly, all radialene compounds having different substitution patterns in structural moieties $A^1$ and $A^2$, are assigned as "asymmetric". This assignment does not encompass the possible geometrical isomers formed by various combinations of E- and Z-substitution on exocyclic double bonds. It is supposed that despite exemplary structures depicted for inventive and comparative radialene compounds prevail, the materials synthesized by described methods may comprise all possible geometric isomers.

Similarly, for the sake of brevity, all possible tautomeric forms and geometric isomers of ester intermediates, betaine intermediates and radialene precursors (reduced forms of desired radialene compounds) are simplified by depicted exemplary structures which, however, in fact represent all isomers and tautomers that are possible in each individual case.

It was found that for any of the tested structures of formula (I) comprising two different aryl and/or heteroaryl substituents in the structural moieties $A^1$ and $A^2$, the dopant strength expressed as redox potential of the compound measured by cyclic voltammetry at standard conditions in acetonitrile solution against Fc/Fc$^+$ reference redox couple, can be within 10% accuracy derived from redox potentials of parent symmetric radialene compounds comprising the aryl/heteroaryl substitution patterns combined in the resulting asymmetric structure.

It was found that each (hetero)aryl-substituted cyanomethylidene structural unit in the [3]-radialene molecule behaves as an independent moiety contributing to overall redox potential by a constant increment which does not depend on the substitution pattern of the (hetero)aryl substituents attached to remaining two corners of the [3]-radialene core. This fact enables an easy prediction of redox potentials for asymmetric structures on the basis of measured redox potentials for "parent" symmetric structures comprising corresponding substitution patterns.

In other words, the redox potential of any asymmetric structure falling within formula (I) can be estimated as a linear combination of increments from structural moieties of corresponding symmetric structures.

The achievement of the object is shown by comparison of properties of inventive compounds with comparative compounds known from the above cited previous art documents or available on the basis of their combined teaching.

The technical effect of the invention can be summarized in three points: The improved radialene p-dopants according to the invention retain good performance of the already known compounds in electronic devices like OLED displays and in semiconducting materials for them and enable robust VTE processes for manufacturing organic electronic devices comprising radialene p-dopants, applicable on the industrial scale.

Specifically, the invention enables adjusting, independently, the doping strength as well as the volatility of the dopant to the dopability and to the volatility of a chosen matrix, in a sufficiently broad range of their values. Moreover, the inventive process for manufacturing of the inventive p-dopants enables their manufacturing in an industrial scale, with more robust quality and higher yields in comparison with the state of the art.

Additionally, wherever the new compound of formula (I) is used instead of a state-of-art p-dopant having smaller redox potential, the stronger p-dopant can be used in lower concentration. It provides additional degrees of freedom for designers of electronic devices, e.g. in terms of lower optical absorption of doped layers which can be provided using the inventive materials in comparison with state-of-art p-dopants.

Exemplary structures of comparative compounds are

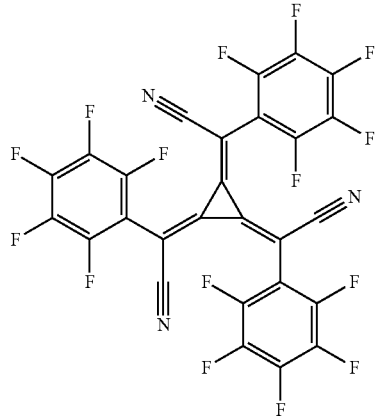

C1

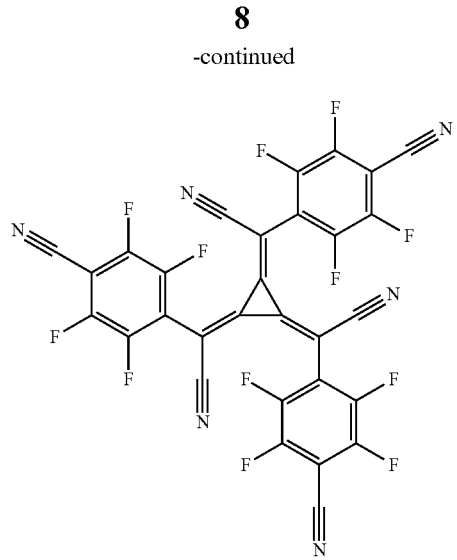

C2

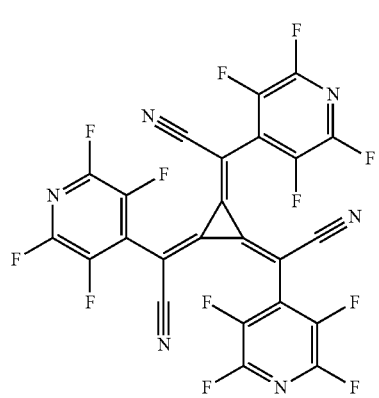

C3

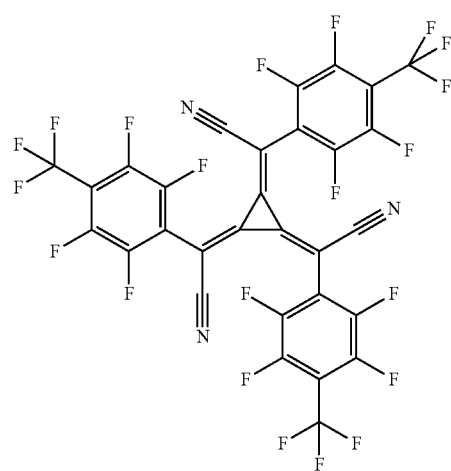

C4

C5
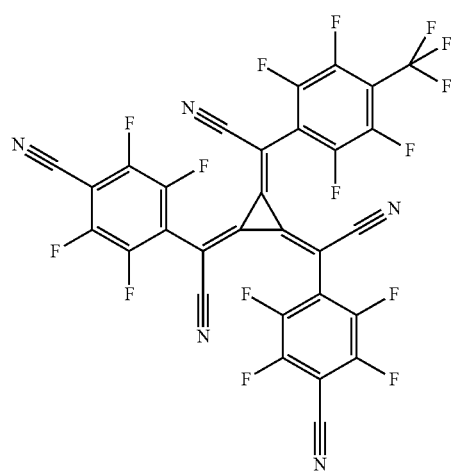
C6
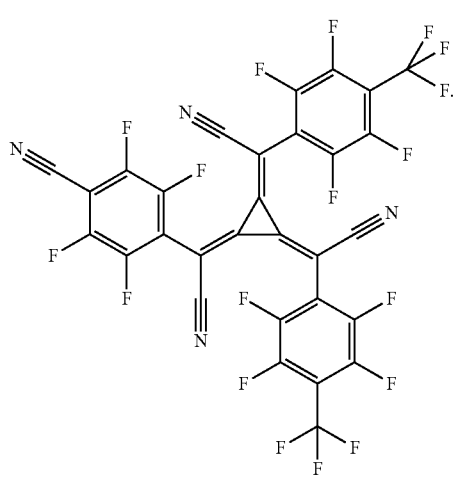
Exemplary Structures of Inventive Compounds
Symmetric Structures
Symmetric structures
A1
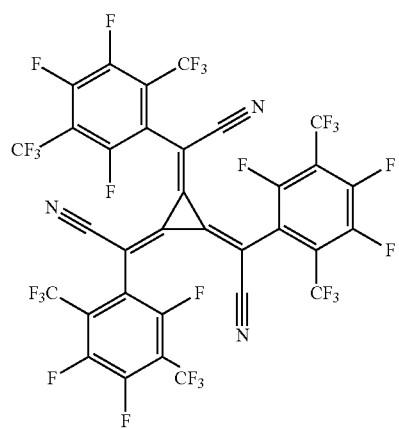
A2
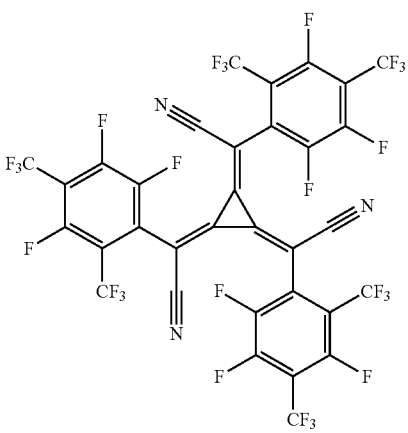
A3
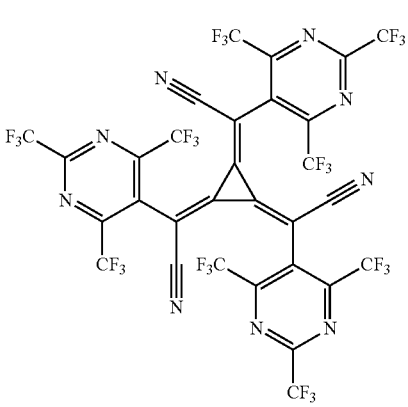
A4
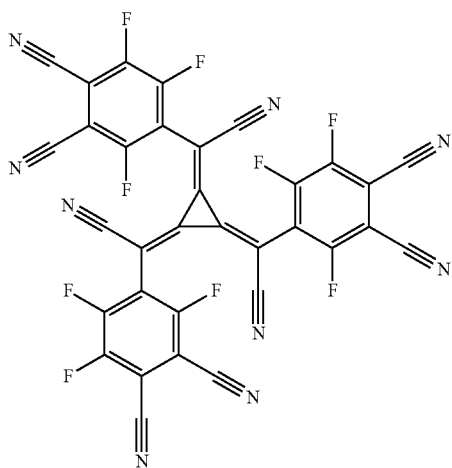

A5
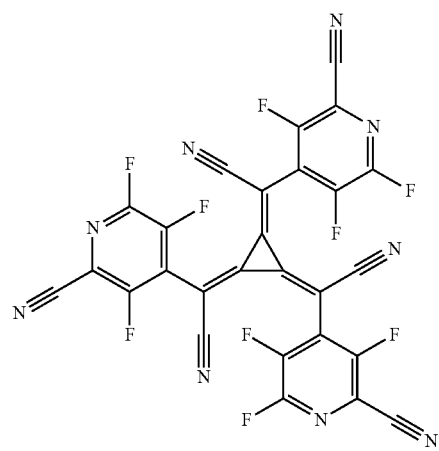
A6
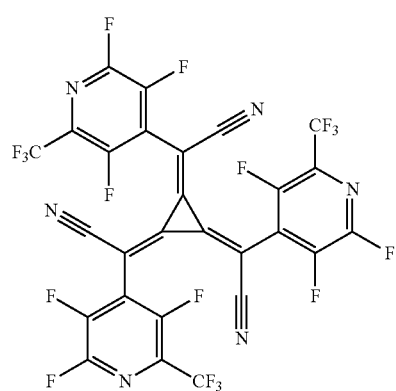
A7
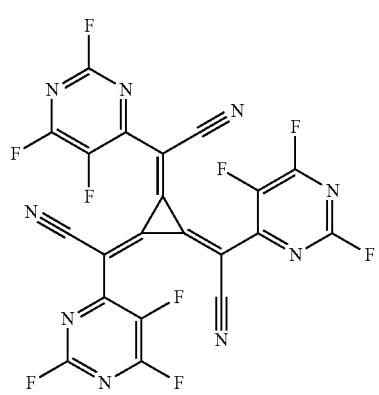
A8
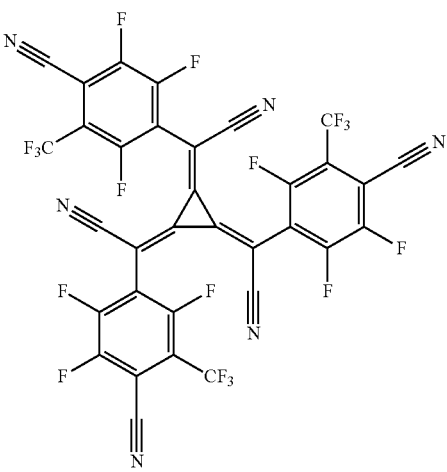
Asymmetric structures
B1
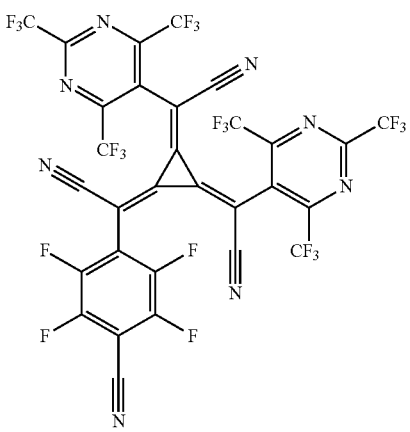
B2
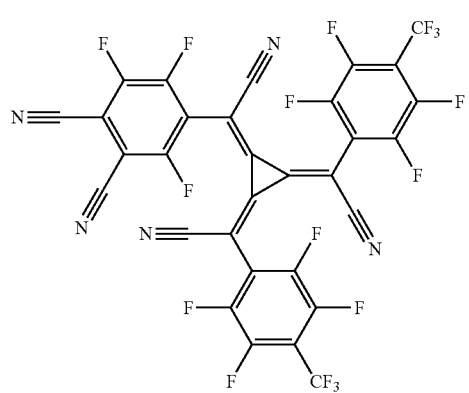

-continued
B3
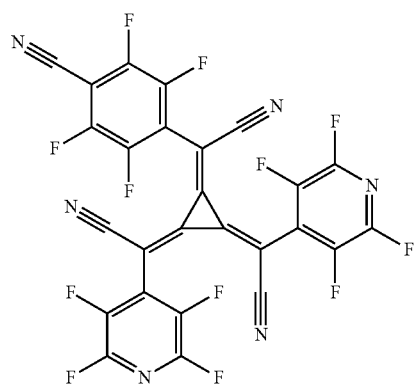
B4
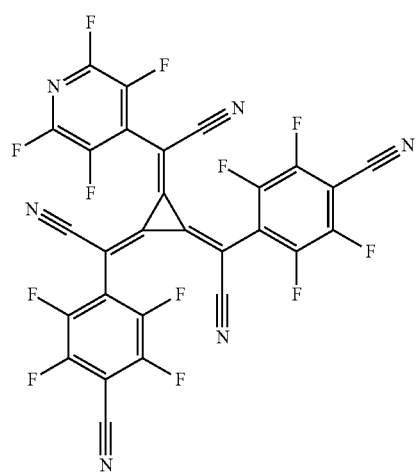
B5
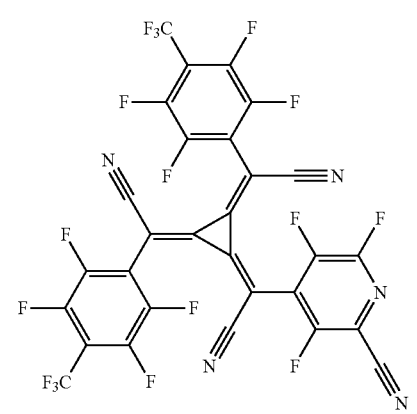
-continued
B6
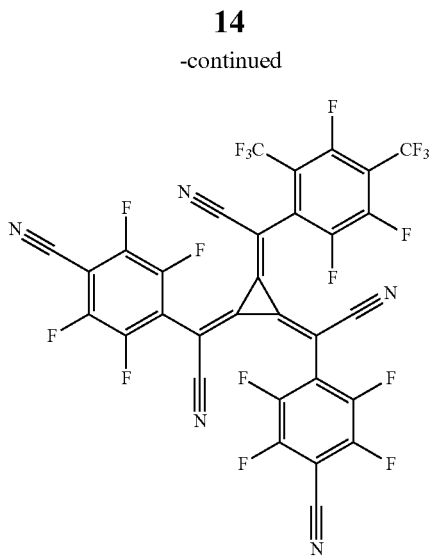
B7
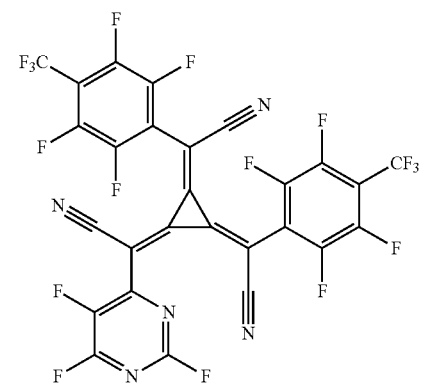
B8
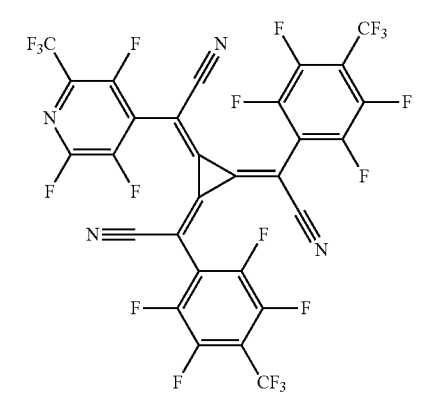

-continued

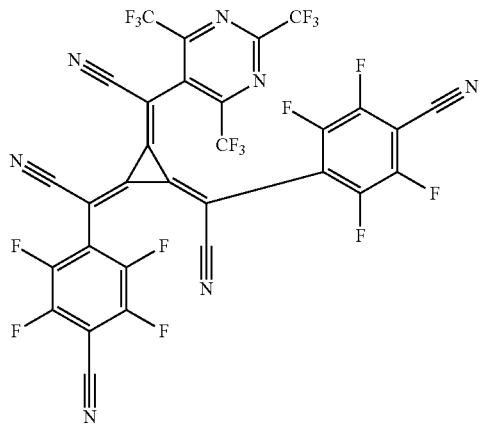
B9

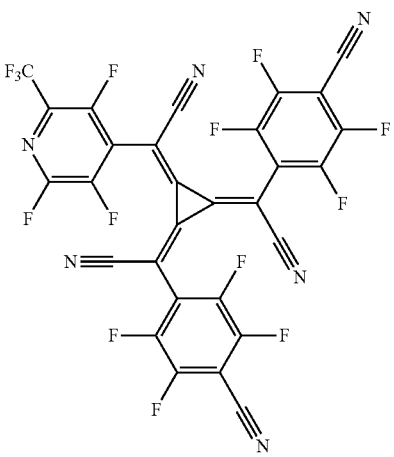
B10

Asymmetric Structures

TABLE 1

| compound | C1 | C2 | C3 | C4 | C5 | C6 | A1 |
|---|---|---|---|---|---|---|---|
| mp (° C.) | 214 | 320 | 122 | 195 | 233 | 212 | 177 |
| $T_{dec}$ (° C.) | 351 | 344 | 329 | 338 | 342 | 340 | 350 |
| $T_{tc}$ (° C.) | 116 | 215 | 127 | 108 | 168 | 142 | — |
| $T_{99.5\%}$ (° C.) | 224 | 321 | 238 | 235 | 280 | 252 | 201 |
| $T_{est}$ (° C.) | 170 | 268 | 182 | 172 | 224 | 197 | 147 |
| $E^0$ (V) | 0.02 | 0.25 | 0.30 | 0.19 | 0.24 | 0.21 | 0.02 |

| compound | A2 | A3 | A4 | A5 | A6 | A7 | A8 |
|---|---|---|---|---|---|---|---|
| mp (° C.) | 179 | 183 | — | — | 206 | 197 | — |
| $T_{dec}$ (° C.) | 360 | — | 365 | — | 333 | 228 | 352 |
| $T_{tc}$ (° C.) | 100 | 77 | 231 | — | 111 | — | — |
| $T_{99.5\%}$ (° C.) | 211 | 164 | 382 | — | 235 | 230 | 302 |
| $T_{est}$ (° C.) | 156 | 120 | 306 | — | 173 | 172 | 231 |
| $E^0$ (V) | 0.18 | 0.38 | 0.33 | 0.39 | 0.34 | 0.46 | 0.29 |

| compound | B1 | B2 | B3 | B4 | B5 | B6 | B7 |
|---|---|---|---|---|---|---|---|
| mp (° C.) | 186 | — | 127 | 132 | — | — | — |
| $T_{dec}$ (° C.) | >300 | 330 | 333 | 333 | 332 | 357 | — |
| $T_{tc}$ (° C.) | 107 | — | — | — | 155 | 142 | — |
| $T_{99.5\%}$ (° C.) | 201 | 280 | 267 | 287 | 261 | 267 | — |
| $T_{est}$ (° C.) | 154 | 212 | 203 | 219 | 208 | 204 | — |
| $E^0$ (V) | 0.33 | 0.24 | 0.28 | 0.26 | 0.26 | 0.23 | — |

| compound | B8 | B9 | B10 |
|---|---|---|---|
| mp (° C.) | — | 203 | — |
| $T_{dec}$ (° C.) | 341 | 359 | 342 |
| $T_{tc}$ (° C.) | — | 116 | — |
| $T_{99.5\%}$ (° C.) | 232 | 252 | 279 |
| $T_{est}$ (° C.) | 176 | 184 | 216 |
| $E^0$ (V) | 0.24 | 0.28 | 0.28 |

Explanations to the Table:

Melting point (mp) temperatures were measured by DSC at heating rate 10 K/min, the reported values correspond the peak temperature for the observed melting endotherm on the DSC curve. $T_{dec}$ stands for the peak temperature of the decomposition peak on the TGA/DSC curve. Two experimentally measured parameters were exploited for estimation of vaporization temperatures that are to be expected in industrial VTE sources used in mass production of OLED displays. The first one, $T_{tc}$, is the evaporation temperature of the compound in a high-vacuum test chamber, provided with a temperature sensor measuring the temperature at the bottom of vaporization crucible filled with a standard amount of the tested compound. The temperature corresponding to the onset of vaporization measured by a detector put above the crucible is reported in the table. The second parameter, $T_{99.5\%}$, corresponds to the temperature at which the TGA curve showed a 0.5% weight loss of the tested compound at normal pressure and 10 K/min heating rate, and it corresponds to the start of compound evaporation at normal pressure. $E^0$ stands for the value of electrochemical redox potential derived from the cyclic voltammetry curves measured in acetonitrile solutions of the tested compounds, against reference redox couple Fc/Fc$^+$ as a standard. All the tested compounds showed reversible redox behavior under these conditions.

It was found that the arithmetic average calculated from the values $T_{tc}$ and $T_{99.5\%}$ for a specific material fits well with the vaporization temperature observed for this material in mass production vaporization sources. For compounds, wherein both values $T_{tc}$ and $T_{99.5\%}$ were available, the estimation of vaporization temperature in the industrial vaporization source $T_{est}$ reported in the table corresponds to this arithmetic average.

For the compounds, wherein only $T_{99.5\%}$ was available, the $T_{est}$ was calculated the same way, only the $T_{tc}$ used in the calculation was the value y calculated from the observed $T_{99.5\%}$ value using the linear relationship y=0.7326*$T_{99.5\%}$-50.084 derived from the correlation between $T_{99.5\%}$ and $T_{tc}$ shown in FIG. 1.

The Table 1 shows that properties of new compounds fulfil the object of the invention, providing a broad spectrum of available redox potentials and vaporization temperatures. For the tested compounds, reasonable long-term thermal stability was proven at vaporization temperatures expected in industrial VTE sources.

It is of course not excluded that the inventive compounds can be advantageous also in processes which are developed as alternatives for VTE, especially in solution processing. It was proven that the new compounds provide not only broad spectrum of volatility but also broad spectrum of solubility in various solvents.

EXAMPLES

Synthesis Examples

Syntheses of symmetric compounds are based on procedures described in U.S. Pat. No. 8,057,712 and application EP 13176542.

Syntheses of asymmetrically substituted derivatives are based on procedures described in U.S. Pat. No. 3,963,769 and in J. Am. Chem. Soc. 1976, volume 98, p. 610-611.
Betaine Precursors
Betaine C2-B A 500 mL Schlenk flask was charged with tetrachlorocyclopropene (8.30 g, 46.7 mmol) and 2-(4-cyano-2,3,5,6-tetrafluorophenyl)acetonitrile (C2-A, 20.0 g, 93.4 mmol) and dry dichloromethane (DCM, 160 mL) were added. The mixture was stirred and cooled to −30° C. and triethyl amine (30.7 g, 304 mmol) was added dropwise over 30 min. The mixture was allowed to warm to room temperature over 1 h. Water (24 mL) was added dropwise and the mixture was filtered. The solid was washed with DCM (3×50 mL), MeOH (2×50 mL) and water (4×50 mL) and dried in vacuum to give 28 g of crude product. Recrystallization from acetonitrile afforded the product as a yellow solid (19 g, 34 mmol).

TGA-DSC (screening): 0.5% mass loss=215° C., Tdec. (onset)=217° C.

ESI/APCI-MS: m/z=532 (M−C$_2$H$_5$).

IR [cm$^{-1}$]: 2987 (w), 2243 (m), 2196 (m), 1851 (m), 1642 (s), 1479 (s), 1422 (s), 1368 (s), 1313 (m), 1200 (m), 1139 (m), 975 (s), 894 (m), 812 (m).

$^{19}$F NMR (471 MHz, CD3CN) δ=−136.53, −141.77.

$^1$H NMR (500 MHz, CD3CN) δ=3.90 (q, 2H), 1.42 (t, 3H).
Betaine C4-B

A 250 mL Schlenk flask was charged with tetrachlorocyclopropene (4.15 g, 23.3 mmol) and 2-(2,3,5,6-tetrafluoro-4-(trifluoromethyl)phenyl)acetonitrile (C4-A, 12.0 g, 46.7 mmol) and dry DCM (80 mL) were added. The mixture was stirred and cooled to −30° C. and triethyl amine (15.4 g, 152 mmol) was added dropwise over 30 min. The mixture was allowed to warm to room temperature over 1 h. Water (12 mL) was added dropwise and the mixture was filtered. The solid was washed with water (2×140 mL) and dried in vacuum to give 6 g of crude product. The filtrate was concentrated to 30 mL upon which a precipitate formed. Filtration gave a second batch of crude product (6 g). Each batch was stirred with diethyl ether (25 mL) for 1 h at room temperature, filtered and the solids were dried in vacuum. The product was obtained as a colorless solid (5.49 g and 5.81 g, equals 11.3 g, 17.5 mmol).

ESI-MS: pos. 436, 648 (M)$^+$, 686; neg. 618 (M-Et-H)$^-$ $^{19}$F NMR (471 MHz, CD3CN) δ=−57.05, −142.79, −144.39.

$^1$H NMR (500 MHz, CD3CN) δ=3.89 (q, 2H), 1.43 (t, 3H).

IR [cm$^{-1}$]: 2996 (w), 2185 (m), 1862 (w), 1652 (m), 1654 (s), 1461 (s), 1419 (s), 1397 (m), 1335 (s), 1316 (m), 1254 (s), 1170 (m), 1150 (m), 1124 (s), 1043 (m), 977 (s), 812 (m).

Analogous betaine intermediates C3-B, A1-B, A2-B, A3-B, A4-B, A5-B, A6-B, A7-B and A8-B which correspond in their substitution to symmetrical radialenes C3, A1, A2, A3, A4, A5, A6, A7 and A8 may be prepared analogously to C2-B and C4-B.
Comparative Compound C5
Radialene Precursor (Reduced Form) C5-P A 500 mL Schlenk flask was charged with betaine C2-B (5.61 g, 10.0 mmol), anhydrous potassium phosphate (4.46 g, 21.0 mmol) and 4-dimethylamino pyridine (1.22 g, 10.0 mmol) under argon. The flask was cooled on ice and dry DMF (185 mL) was added. The mixture was stirred on ice for 10 minutes and a solution of 2-(2,3,5,6-tetrafluoro-4-(trifluoromethyl) phenyl)acetonitrile C4-A (2.70 g, 10.5 mmol) in DMF (15 mL) was added over 10 minutes. After 4 h stirring on ice, the cooling bath was removed and the mixture allowed to warm to room temperature. After a total reaction time 27 h, the black-red mixture was added to brine (150 mL) and EtOAc (400 mL). The phases were separated and the organic layer was washed with half-concentrated brine (2×150 mL), 2 M aqueous HCl (3×150 mL) (solution turns dark green) and saturated aqueous NaHCO3 (3×100 mL) (solution turns black/red). The organic phase was dried over MgSO4 and concentrated. Column chromatography (silica gel) with DCM/MeOH provided a dark red solution which was concentrated to give the product as a black solid (4.88 g).

This intermediate was not further purified, it was directly used in the last step.
Radialene C5

Precursor C5-P (4.82 g) was dissolved in glacial acetic acid (67 mL) and aqueous nitric acid (65% w/w, 67 mL) was added dropwise at room temperature. The solution turned from black/green to red/orange. After stirring for 16 h, an orange precipitate formed and the mixture was cooled on ice. Water (70 mL) was added dropwise and the mixture was stirred for 15 min. Filtration gave an orange solid which was washed with cold water (10×40 mL) until the filtrate is neutral. Drying in air and in oil pump vacuum gave 3.25 g of a solid which was dissolved in hot 1-chlorobutane (100° C., 400 mL). The solution was cooled to room temperature and filtered through a glass frit. The filtrate was concentrated to approx. 50 mL to give a suspension comprising an orange solid. After filtration and drying in air and in oil pump vacuum, the product was obtained as an orange powder (2.62 g) and further purified by sublimation in high vacuum.

ESI-MS: m/z=715 (neg.)

UV-Vis (acetonitrile (ACN)): $\lambda_{max}$=457 nm.

IR [cm$^{-1}$]: 2249 (w), 1662 (w), 1563 (m), 1486 (s), 1415 (m), 1343 (m), 1328 (m), 1257 (m), 1194 (m), 1155 (m), 1069 (m), 978 (s), 909 (m), 813 (m), 717 (m).

TGA-DSC (volatility): 0.5% mass loss at 281° C., $T_{dec.}$ (onset)=325° C.

$^{19}$F NMR (471 MHz, CH3CN): δ=−57.43, −77.04, −132.42, −134.43, −135.08, −139.98.

Comparative Compound C6

Radialene Precursor (Reduced Form) C6-P

A 250 mL Schlenk flask was charged with $Cs_2CO_3$ (3.42 g, 10.5 mmol) and DMF (90 mL). The mixture was stirred on ice for 10 minutes and betaine C4-B (3.24 g, 5.0 mmol) was added. After 10 minutes, a solution of 2-(4-cyano-2,3,5,6-tetrafluorophenyl)acetonitrile C2-A (1.09 g, 5.1 mmol) in DMF (10 mL) was added. The mixture was stirred on ice and the cooling bath was removed after 19 h. After a total reaction time of 1 d 19 h, the black-red mixture was added to brine (80 mL) and EtOAc (200 mL). The phases were separated and the organic layer was washed with half-concentrated brine (2×80 mL), dried over $MgSO_4$ and concentrated to give the product as black-red oil containing some residual DMF (6.29 g).

This intermediate was not further purified, it was directly used in the last step.

Radialene C6

Precursor C6-P (6.29 g) was dissolved in 83 mL glacial acetic acid and 83 mL aqueous nitric acid (65% w/w) were added dropwise at room temperature. The solution turned from black-green to red-orange. After stirring for 16 h, an orange precipitate has formed and the mixture was cooled on ice. 100 mL water were added dropwise and the mixture was stirred for 15 min. Filtration gave an orange solid which was washed with cold water (8×30 mL) until the filtrate was neutral. After drying in air and in oil pump vacuum, the product was obtained as an orange powder (3.07 g) which was further purified by sublimation in high vacuum.

ESI-MS: m/z=758 (neg.)

UV-Vis (ACN): $\lambda_{max}$=454 nm.

IR [cm$^{-1}$]: 2248 (w), 1662 (w), 1565 (m), 1483 (s), 1416 (m), 1339 (s), 1252 (m), 1198 (m), 1148 (s), 1060 (m), 984 (s), 907 (m), 812 (m), 785 (w), 715 (m).

TGA-DSC (volatility): 0.5% mass loss at 252° C., $T_{dec.}$ (onset)=320° C.

$^{19}$F NMR (471 MHz, CD3CN) δ=−57.46, −132.46, −134.50, −135.15, −140.04.

Inventive Compound B5

Step 1: potassium 1-cyano-1-(2-cyano-3,5,6-trifluoropyridin-4-yl)-2-ethoxy-2-oxoethan-1-ide (Ester Intermediate A3-eE)

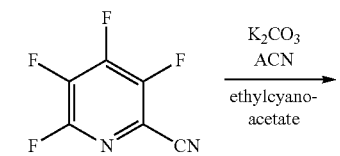

Chemical Formula: $C_6F_4N_2$
Molecular Weight: 176.07

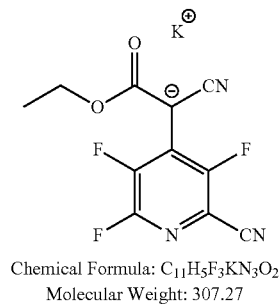

Chemical Formula: $C_{11}H_5F_3KN_3O_2$
Molecular Weight: 307.27

In a 250 mL flask, to 7.2 g (142 mmol) 2-cyano-3,4,5,6-tetrafluoropyridine, 60 mL acetonitrile and 6.78 g (170.4 mmol) potassium carbonate, 4.6 g (142 mmol) ethyl cyano acetate, dissolved in 10 mL ACN, were added. After 3 days stirring at room temperature, the formed precipitate was filtered and washed with 2×20 mL ACN. The organic solvent was evaporated. The remaining orange solid was dried in vacuum (10$^{-3}$ mbar) and used in the next step without any further purification.

Yield: 10.4 g (83%)

ESI-MS: M (neg)=268.

HPLC-MS m/z=268 (neg.).

Step 2:
4-(cyanomethyl)-3,5,6-trifluoropicolinonitrile (Nitrile Intermediate A3-A)

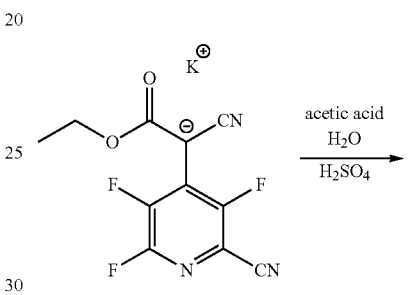

Chemical Formula: $C_{11}H_5F_3KN_3O_2$
Molecular Weight: 307.27

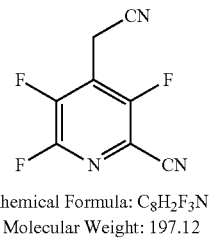

Chemical Formula: $C_8H_2F_3N_3$
Molecular Weight: 197.12

In a 250 mL round bottom flask, 10.39 g (33.8 mmol) ester intermediate A3-eE were dissolved in 86 mL aqueous acetic acid (50% w/w). 1.3 mL sulphuric acid (conc.) were added and the mixture was heated under reflux for 2 hours. After cooling to room temperature, the mixture was poured into a 1 L beaker with 200 mL ice water. After adding 200 mL ethyl acetate, the mixture was stirred over a period of 30 min at room temperature. The organic layer was separated and the aqueous layer extracted with 2×200 mL ethyl acetate. The combined organic layers were washed with 200 mL water, 200 mL saturated aqueous sodium bicarbonate solution and 200 mL water. After drying over sodium sulphate, the solvent was removed in vacuum from the solution, to give yellow coloured oil. Distillation in vacuum gave a slight yellow oil ($T_{bath}$: 190° C.; bp: 110° C. at 4*10$^{-3}$ mbar).

Yield: 4.5 g (68%).

TLC (SiO$_2$, DCM): $R_f$=0.65

GC-MS: $t_R$=9.02 min., m/z=197, 95%; $t_R$=8.86 min., m/z=197, 5%.

$^1$H-NMR (600 MHz, CD$_3$CN): δ=4.03 (s, 2H).

$^{19}$F-NMR (282 MHz, CD$_3$CN): δ=−81.11 (t, J=25.4, 1F), −114.21 (dd, J=8.1, 26.5, 1F), −122.46 (dd, J=8.0, 24.3, 1F).

Step 3: (Z)-4-(cyano(2-(cyano(2,3,5,6-tetrafluoro-4-(trifluoromethyl)-phenyl)methyl)-3-(cyano(2,3,5,6-tetrafluoro-4-(trifluoromethyl)phenyl)-methylene)cycloprop-1-en-1-yl)methyl)-3,5,6-trifluoropicolinonitrile (Radialene Precursor B5-P)

Step 4: (2Z,2'E)-2,2'-((E)-3-(cyano(2-cyano-3,5,6-trifluoropyridin-4-yl)methylene)cyclopropane-1,2-diylidene)bis(2-(2,3,5,6-tetrafluoro-4-(trifluoromethyl)-phenyl)acetonitrile)

(Radialene Compound B5)

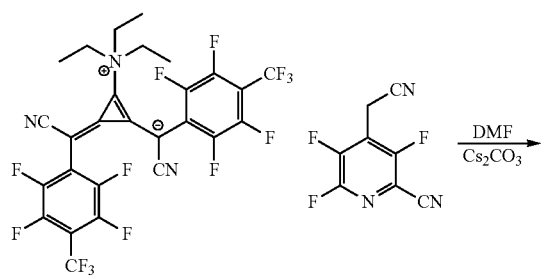

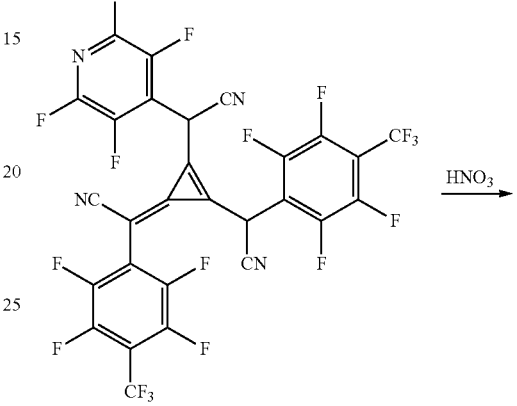

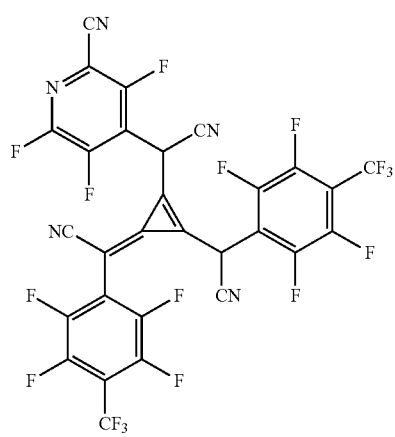

In a 250 mL Schlenk flask under argon, 3.3 g Cs$_2$CO$_3$ were suspended in 90 mL DMF. The suspension was cooled to 0° C. and 3.1 g (4.8 mmol) betaine intermediate C4-B were added upon which an orange suspension formed. After addition 1.0 g 4-(cyanomethyl)-3,5,6-trifluoropicolinonitrile (A3-A, 5.0 mmol) in 10 mL dry DMF at 0° C., the cooling bath was removed and stirring continued overnight. The brown suspension was stirred at room temperature for additional 24 hours, and the mixture was poured into 100 mL saturated NaCl solution. Extraction with 100 mL ethyl acetate, washing two times with 50 ml aqueous NaCl solution, drying with Na$_2$SO$_4$ and removal of the solvent yielded a red oil which was dried in vacuum.

Crude yield: 6.89 g (191%)

HPLC-MS: m/z=371 ((nm/z)/2), 742 (m/z–H, C$_{29}$H$_1$F$_{17}$N$_5^{2-}$), t$_R$=7.8 min., m/z=741 (m/z–H, C$_{29}$F$_{17}$N$_5^-$), t$_R$=13.9 min.

3.3 g (1.0 mmol) radialene precursor B5-P were dissolved in 44 mL glacial acetic acid and treated dropwise at room temperature with 44 mL aqueous nitric acid (65% w/w). The resulting red solution was stirred overnight and afterwards poured into 80 mL cold water. After 1 h stirring at room temperature, the resulting orange precipitate was filtered off, washed with water until pH was neutral and dried in vacuum.

Yield: 1.26 g (39%)

The crude product was recrystallized from a mixture of cyclohexane and chlorohexane.

Inventive Compound B6

Step 1: ethyl 2-cyano-2-(2,3,5-trifluoro-4,6-bis(trifluoromethyl)phenyl)acetate potassium salt (Ester Intermediate A2-eE)

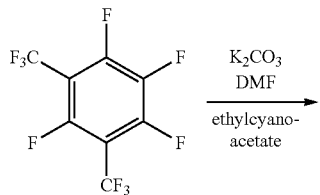

Chemical Formula: $C_8F_{10}$
Molecular Weight: 286.07

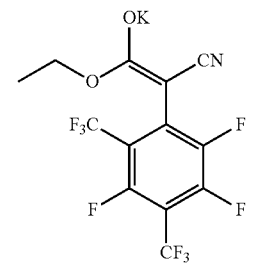

Chemical Formula: $C_{13}H_5F_9KNO_2$
Molecular Weight: 417.27

In a 250 mL flask, 10 g perfluor-m-xylene, 65 mL DMF and 5.8 g anhydrous potassium carbonate were mixed. After 5 min. stirring, 3.75 mL ethyl cyanoacetate were added dropwise to the continuously stirred yellow suspension. After 48 h at room temperature, the reaction was complete according to TLC-analysis. The precipitate formed during the reaction was removed by filtration and washed with acetonitrile. The filtrate was rotary evaporated to dryness and the resulting oil was dissolved in 40 mL toluene and again evaporated to dryness in order to remove residual DMF.

Crude yield: 18.8 g (129%)
ESI-MS: m/z=378 (m/z–K, $C_{13}H_5F_9NO_2^-$; neg.)
IR (ATR): 3443, 2161, 1662, 1599, 1469, 1352, 1262, 1215, 1125, 1062, 936, 879, 732 cm$^{-1}$.

Step 2: 2-(2,3,5-trifluoro-4,6-bis(trifluoromethyl)phenyl)acetonitrile (Nitrile Intermediate A2-A)

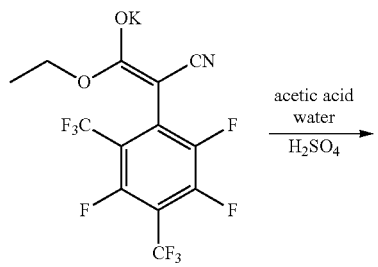

Chemical Formula: $C_{13}H_5F_9KNO_2$
Molecular Weight: 417.27

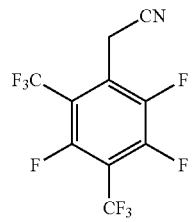

Chemical Formula: $C_{10}H_2F_9N$
Molecular Weight: 307.12

In a 250 mL flask, 18.0 g crude ethyl 2-cyano-2-(2,3,5-trifluoro-4,6-bis(trifluoromethyl)phenyl)acetate potassium salt (A2-eE from the previous step) and 4.6 mL conc. sulphuric acid were dissolved in aqueous acetic acid (50% v/v). The mixture was heated under reflux for 48 hours. After cooling to room temperature, the mixture was poured into a 500 mL beaker with 100 mL ice water and stirred over a period of 5 min. The mixture was extracted with 3×50 mL ethyl acetate. The combined organic layers were washed with 2×50 mL saturated sodium bicarbonate aqueous solution and with 100 mL water. After drying the organic layer with sodium sulphate, the solvent was removed in vacuum to give a brown coloured oil. Distillation in vacuum gave a colourless liquid (bp: 75-80° C. (at ($10^{-2}$ mbar; main fraction).

Yield: 8.45 g (64%).

GC-MS: m/z=307.

IR (ATR): 1650, 1608, 1495, 1469, 1354, 1243, 1142, 1081, 1033, 963, 894, 733, 655 cm$^{-1}$.

Step 3: 4-(cyano(2-(cyano(2,3,5-trifluoro-4,6-bis(trifluoromethyl)phenyl)-methyl)-3-(cyano(4-cyano-2,3,5,6-tetrafluorophenyl)methyl)cycloprop-2-en-1-ylidene)-methyl)-2,3,5,6-tetrafluorobenzonitrile (Radialene Precursor B6-P)

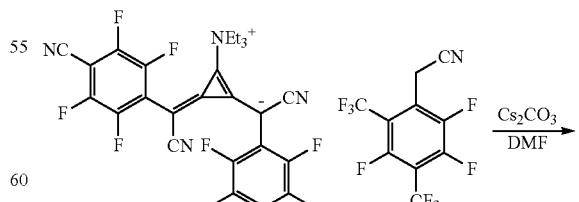

Chemical Formula: $C_{27}H_{15}F_8N_5$
Molecular Weight: 561.45

Chemical Formula: $C_{10}H_2F_9N$
Molecular Weight: 307.12

-continued

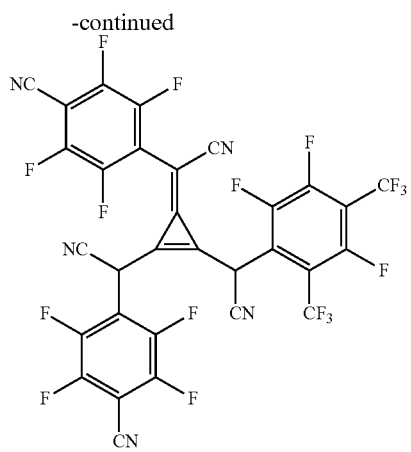

Chemical Formula: $C_{31}H_2F_{17}N_5$
Molecular Weight: 767.36

In a 100 mL Schlenk flask under argon, 2.12 g cesium carbonate were suspended in 45 mL dry dimethyl formamide and cooled to 0° C. To the suspension, a solution of 1.0 g 2-(2,3,5-trifluoro-4,6-bis(trifluoromethyl)phenyl)acetonitrile in 5 mL dry dimethyl formamide was slowly added. The mixture was stirred for 5 min and 1.74 g of betaine intermediate C2-B were added as a solid. The stirring continued for 24 h and the reaction was allowed to reach ambient temperature. The reaction mixture was poured into a 250 mL separatory funnel containing 100 mL water and 80 mL ethyl acetate. The organic layer was separated, washed twice with 80 mL half-saturated NaCl aqueous solution, twice with 80 mL 2 M aqueous HCl, and twice with 80 mL saturated aqueous sodium bicarbonate solution.

The organic layer was finally dried with magnesium sulphate and the solvent was carefully removed by vacuum evaporation to give a dark purple solid.

Crude yield: 2.8 g (115%).
ESI-MS: m/z=766, 382 (neg.).
IR (ATR): 2233, 2165, 1639, 1475, 1370, 1339, 1257, 1214, 1134, 969, 815, 732 cm$^{-1}$.

Step 4: (4,4'-((1Z,1'E)-((E)-3-(cyano(3,5,6-trifluoro-2,4-bis(trifluoromethyl)phenyl) methylene)cyclopropane-1,2-diylidene)bis(cyanomethanylylidene))bis(2,3,5,6-tetrafluorobenzonitrile)
(Radialene Compound B6)

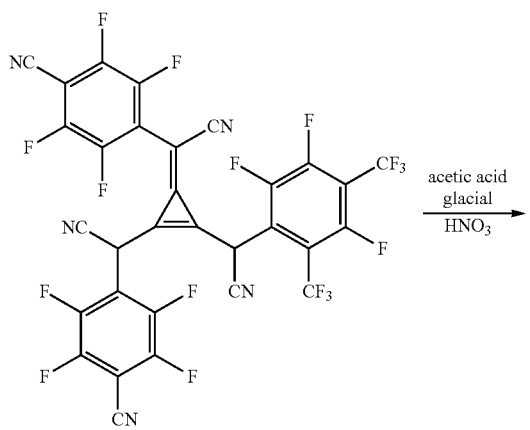

Chemical Formula: $C_{31}H_2F_{17}N_5$
Molecular Weight: 767.36

-continued

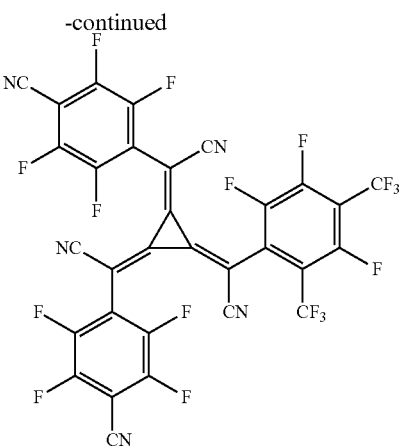

Chemical Formula: $C_{31}F_{17}N_5$
Molecular Weight: 765.35

In a 100 mL flask equipped with a dropping funnel, 1.44 g (1.88 mmol) radialene precursor B6-P were dissolved in 19 mL glacial acetic acid. Under vigorous stirring, 19 mL concentrated nitric acid (65%, w/w) were added dropwise. During the nitric acid addition, the color of the solution changed from a greenish yellow to dark red. Stirring was continued overnight.

The solution was then cooled to 0° C. and 40 mL water were added dropwise to induce precipitation of the bright orange product. The crude solid product was collected on sintered glass frit and washed with 3×15 mL water. The wet raw material was dried in a vacuum drying cabinet at 40° C. for 3 h and then at ambient temperature in high vacuum (10$^{-2}$ mbar). The dried material was then recrystallized from 3:2 (v/v) mixture of 1-chlorobutane and cyclohexane.

Yield: 333 mg (23%)
Inventive Compound B7

Step 1: Potassium 2-(tert-butoxy)-1-cyano-2-oxo-1-(2,5,6-trifluoropyrimidin-4-yl)ethan-1-ide (Ester Intermediate A7-tbE)

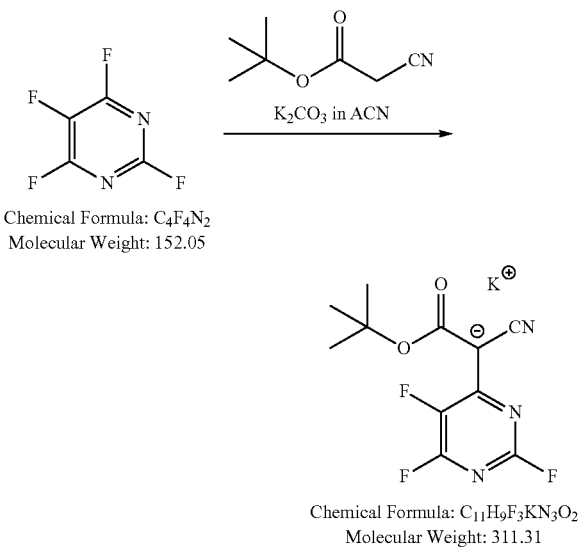

In a 250 mL flask, 10 g (65.8 mmol) perfluoropyrimidine and 18.2 g (132 mmol) anhydrous potassium carbonate were dissolved/suspended in 130 mL acetonitrile. A solution of 11.14 g (78.9 mmol) tert-butyl 2-cyanoacetate in 10 mL acetonitrile was added under stirring, a colorchange of the reaction mixture to yellow was observed. The reaction mixture was stirred for 3 days at ambient temperature and filtered to remove solids. The solvent was removed from the filtrate and the obtained yellow solid was triturated with 120 mL DCM.

Yield: 20.1 g (98%)

$^{1}$H-NMR (CD$_3$CN, 300 MHz): 1.47 (s, 9H).

$^{19}$F-NMR (CD$_3$CN, 282.3 MHz): −53.2 (d, 1F), −93.4 (d, 1F), −163.7 (br s, 1F).

IR (ATR, cm$^{-1}$): 2185, 1738, 1646, 1606, 1539, 1461, 1442, 1377, 1281, 1198, 1155, 1115, 1027, 899, 840, 775.

Step 2: 2-(2,5,6-trifluoropyrimidin-4-yl)acetonitrile (Nitrile Intermediate A7-A)

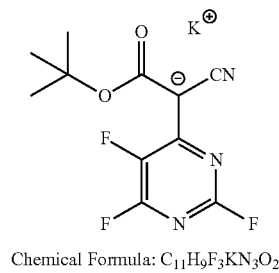

Chemical Formula: C$_{11}$H$_9$F$_3$KN$_3$O$_2$
Molecular Weight: 311.31

HCl in dioxane →

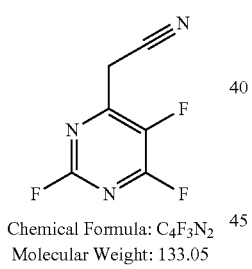

Chemical Formula: C$_4$F$_3$N$_2$
Molecular Weight: 133.05

A pressure tube with a screw cap was charged with 5.5 g (17.7 mmol) A7-tbE and 60 mL dioxane. To this mixture, 17.7 mL 4 M anhydrous HCl in dioxane were added and the tube was sealed. The reaction mixture was heated for 4 h to 100° C. and subsequently poured into 100 mL water. This mixture was extracted with 3×50 mL EtOAc and the collected organic layers washed with 50 mL water and 50 mL brine. After drying with Na$_2$SO$_4$, the solvent was removed and the crude product was purified by bulb-to-bulb distillation (140° C. @ 3×10$^3$ mbar).

Yield: 2.02 g (66%)

$^{19}$F-NMR (CDCl$_3$, 282.3 MHz): −45.2 (d, 1F), −72.3 (d, 1F), −156.2 (m, 1F).

GC-MS: m/z=173 (M$^+$, 100), 153 (20), 108 (20)

IR (ATR, cm$^{-1}$): 2269, 1609, 1462, 1402, 1243, 1105, 1050, 1017, 928, 769, 725.

Step 3: (Z)-2-(2-(cyano(2,3,5,6-tetrafluoro-4-(trifluoromethyl)phenyl)-methyl)-3-(cyano(2,3,5,6-tetrafluoro-4-(trifluoromethyl)phenyl)methylene)cycloprop-1-en-1-yl)-2-(2,5,6-trifluoropyrimidin-4-yl) acetonitrile (Radialene Precursor B7-P)

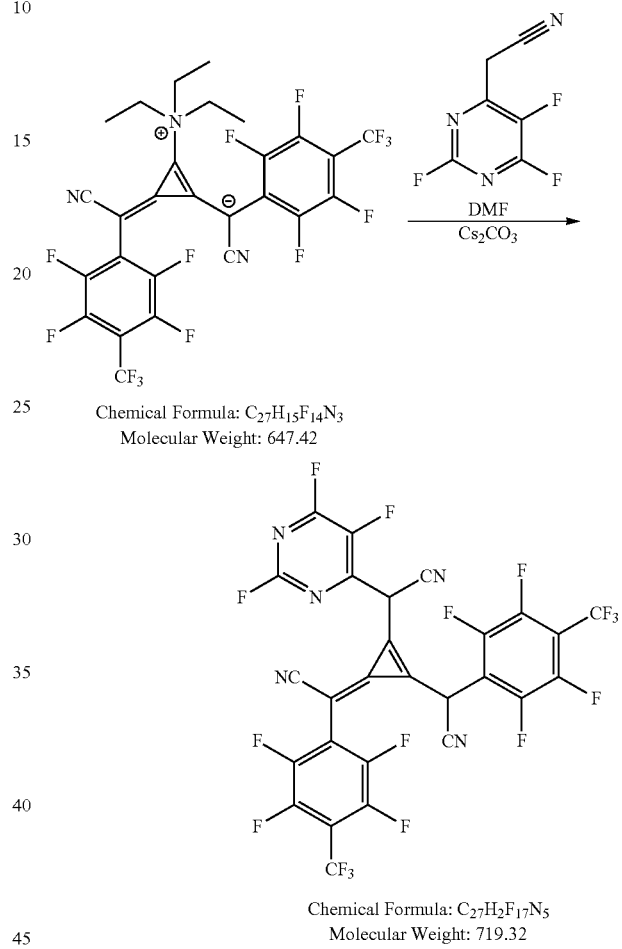

In a 250 mL Schlenk flask under argon, 3.6 g Cs$_2$CO$_3$ were suspended in 90 mL DMF. The suspension was cooled to 0° C. and betaine intermediate C4-B (3.6 g, 5.6 mmol) was added upon which an orange suspension formed. After an addition of 1.0 g 2-(2,5,6-trifluoropyrimidin-4-yl)acetonitrile (A7-A, 5.7 mmol) in 10 mL dry DMF to the stirred mixture at 0° C., the cooling bath was removed and stirring was continued overnight. The brown suspension was stirred at room temperature for additional 24 hours, and the reaction mixture was then poured into 100 mL saturated aqueous NaCl solution. Extraction with 100 mL ethyl acetate, washing two times with 50 mL NaCl-solution, drying with Na$_2$SO$_4$ and removal of the solvent afforded a red oil which was dried in vacuum.

Crude yield: 6.06 g (151%).

HPLC-MS: m/z=358 ((m/z)/2), 718 (M-H).

Step 4: (2Z,2'E)-2,2'-((E)-3-(cyano(2,5,6-trifluoro-pyrimidin-4-yl)methylene)-cyclpropane-1,2-di-ylidene)bis(2-(2,3,5,6-tetrafluoro-4-(trifluoromethyl)phenyl)-acetonitrile)

(Radialene Compound B7)

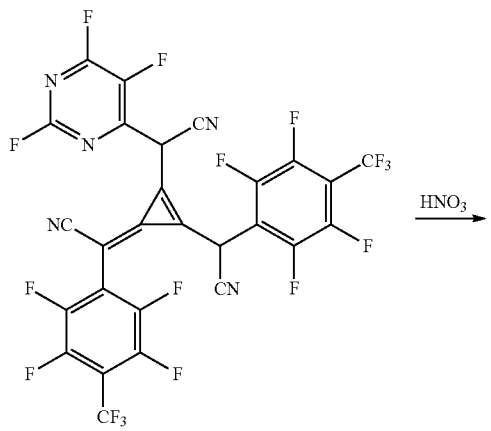

Chemical Formula: C$_{27}$H$_2$F$_{17}$N$_5$
Molecular Weight: 719.32

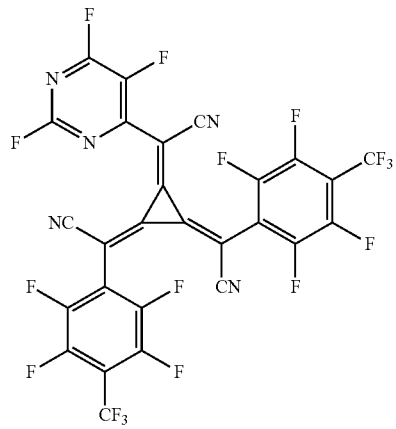

Chemical Formula: C$_{27}$F$_{17}$N$_5$
Molecular Weight: 717.30

3.0 g (4.2 mmol) A7-P were dissolved in 42 mL glacial acetic acid and treated dropwise at room temperature with 42 mL aqueous nitric acid (65% w/w). The resulting red solution was stirred overnight and afterwards poured into 80 mL cold water. After 1 h stirring at room temperature, the resulting orange precipitate was filtered off, washed with water until pH was neutral and dried in vacuum.

Crude yield: 0.9 g (30%)

The crude product was recrystallized from a mixture of cyclohexane and chlorohexane.

Device Example

In an experimental OLED built on a glass substrate provided with an ITO anode, 10 nm thick hole injection transport layer (HIL) consisting of commercially available biphenyl-4-yl(9,9-diphenyl-9H-fluoren-2-yl)-[4-9-phenyl-9H-carbazol-3-yl)phenyl]-amine (CAS number 1242056-42-3) doped with 8 weight % of the tested compound, 130 nm thick hole transport layer made of the same matrix compound as the HIL, 20 nm thick emitting layer made of commercially available host compound ABH113 with 3 wt % emitter NUBD370 (both from the same supplier Sun Fine Chemicals, Korea), 36 nm thick electron transport layer made of (3-(dibenzo[c,h]acridin-7-yl)phenyl)diphenylphosphine oxide and lithium 8-hydroxyquinolinolate (LiQ, 1:1 w/w), and 30 nm thick silver cathode, similar performance in terms of voltage, efficiency, lifetime and color coordinates was observed for comparative and inventive compounds.

The features of the invention which are disclosed in the previous description and in the claims individually, can be used as well as in any combination for the realization of the invention in its various embodiments.

Abbreviations and symbols used throughout the application
ACN acetonitrile
bp boiling point
br broad
CAS Chemical Abstract Service
conc. concentrated
CV cyclic voltammetry
DCM dichloromethane
DMF N,N-dimethylformamide
DSC differential scanning calorimetry
E$^0$ electrochemical redox potential
EIL electron injecting layer
ESI electrospray ionization
ETL electron transporting layer
ETM electron transport matrix
EtOAc ethyl acetate
Fc$^+$/Fc ferricenium/ferrocene reference system
GC gas chromatography
HIL hole injecting layer
HOMO highest occupied molecular orbital
HTL hole transporting layer
HTM hole transport matrix
IR infrared (light, spectroscopy)
ITO indium tin oxide
LiQ lithium 8-hydroxyquinolinolate
LUMO lowest unoccupied molecular orbital
mol % molar percent
MeOH methanol
mp melting point
MS mass spectrometry
m/z mass/charge ratio
neg. negative
OLED organic light emitting diode
R$_f$ retention factor
TGA thermogravimetric analysis
THF tetrahydrofuran
TLC thin layer chromatography
t$_r$ retention time
UV-vis ultraviolet-visible (light, spectroscopy)
vol % volume percent
v/v volume-to-volume (volume percent)
VTE vacuum thermal evaporation
wt % weight (mass) percent
w/w weight-to-weight (mass percent)

The invention claimed is:
1. A process for preparation of an electrically doped semiconducting material comprising a [3]-radialene p-dopant or for preparation of an electronic device including a layer comprising a [3]-radialene p-dopant, the process comprising the steps:
(i) loading an evaporation source with the [3]-radialene p-dopant and
(ii) evaporating the [3]-radialene p-dopant at an elevated temperature and at a reduced pressure, wherein the [3]-radialene p-dopant is selected from compounds having a structure according to formula (I)

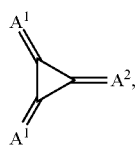
(I)

wherein $A^1$ and $A^2$ are independently aryl- or heteroaryl-substituted cyanomethylidene groups,
the aryl and/or heteroaryl is selected independently in $A^1$ and $A^2$ from 4-cyano-2,3,5,6-tetrafluorphenyl, 2,3,5,6-tetrafluorpyridine-4-yl, 4-trifluormethyl-2,3,5,6-tetrafluorphenyl, 2,4-bis(trifluormethyl)-3,5,6-trifluorphenyl, 2,5-bis(trifluormethyl)-3,4,6-trifluorphenyl, 2,4,6-tris(trifluormethyl)-1,3-diazine-5-yl, 3,4-dicyano-2,5,6-trifluorphenyl, 2-cyano-3,5,6-trifluorpyridine-4-yl, 2-trifluormethyl-3,5,6-trifluorpyridine-4-yl, 2,5,6-trifluor-1,3-diazine-4-yl and 3-trifluormethyl-4-cyano-2,5,6-trifluorphenyl,
and at least one aryl or heteroaryl is 2,3,5,6-tetrafluorpyridine-4-yl, 2,4-bis(trifluormethyl)-3,5,6-trifluorphenyl, 2,5-bis(trifluormethyl)-3,4,6-trifluorphenyl, 2,4,6-tris(trifluormethyl)-1,3-diazine-5-yl, 3,4-dicyano-2,5,6-trifluorphenyl, 2-cyano-3,5,6-trifluorpyridine-4-yl, 2-trifluormethyl-3,5,6-trifluorpyridine-4-yl, 2,5,6-trifluor-1,3-diazine-4-yl or 3-trifluormethyl-4-cyano-2,5,6-trifluorphenyl,
provided that the heteroaryl in both $A^1$ and $A^2$ cannot be 2,3,5,6-tetrafluorpyridine-4-yl at the same time.

2. The process according to claim 1, wherein the temperature in step (ii) is in the range 100-300° C.

3. The process according to claim 1, wherein the duration of the step (ii) is at least 100 hours.

4. The process according to claim 1, wherein in the step (ii), a hole transport material comprising at least one hole transport matrix compound is co-evaporated with the compound having structure (I) and, in a subsequent step (iii), the compound (I) and the hole transport matrix compound are co-deposited to form a semiconducting material.

5. The process according to claim 1, wherein the step (ii) is carried out at a pressure which is lower than $10^{-1}$ Pa.

6. The process according to claim 1, wherein compound (I) has reversible redox potential, measured by cyclic voltammetry in acetonitrile against ferrocene/ferricenium reference system, in the range from +0.10 to +0.50 V.

7. A [3]-radialene compound having a structure according to formula (I):

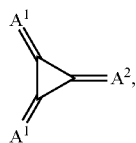
(I)

wherein
$A^1$ and $A^2$ are independently aryl- or heteroaryl-substituted cyanomethylidene groups, the aryl and/or heteroaryl is selected independently in $A^1$ and $A^2$ from 4-cyano-2,3,5,6-tetrafluorphenyl, 2,3,5,6-tetrafluorpyridine-4-yl, 4-trifluormethyl-2,3,5,6-tetrafluorphenyl, 2,4-bis(trifluormethyl)-3,5,6-trifluorphenyl, 2,5-bis(trifluormethyl)-3,4,6-trifluorphenyl, 2,4,6-tris(trifluormethyl)-1,3-diazine-5-yl, 3,4-dicyano-2,5,6-trifluorphenyl, 2-cyano-3,5,6-trifluorpyridine-4-yl, 2-trifluormethyl-3,5,6-trifluorpyridine-4-yl, 2,5,6-trifluor-1,3-diazine-4-yl and 3-trifluormethyl-4-cyano-2,5,6-trifluorphenyl,
and at least one aryl or heteroaryl is 2,3,5,6-tetrafluorpyridine-4-yl, 2,4-bis(trifluormethyl)-3,5,6-trifluorphenyl, 2,5-bis(trifluormethyl)-3,4,6-trifluorphenyl, 2,4,6-tris(trifluormethyl)-1,3-diazine-5-yl, 3,4-dicyano-2,5,6-trifluorphenyl, 2-cyano-3,5,6-trifluorpyridine-4-yl, 2-trifluormethyl-3,5,6-trifluorpyridine-4-yl, 2,5,6-trifluor-1,3-diazine-4-yl or 3-trifluormethyl-4-cyano-2,5,6-trifluorphenyl,
provided that the heteroaryl in both $A^1$ and $A^2$ cannot be 2,3,5,6-tetrafluorpyridine-4-yl at the same time.

8. The compound according to claim 7, having reversible redox potential, measured by cyclic voltammetry in acetonitrile against ferrocene/ferricenium reference system, in the range from +0.10 to +0.50 V.

9. A semiconducting material comprising the compound according to claim 7 and a matrix material comprising at least one hole transport matrix compound.

10. An electronic device comprising, between a first and a second electrode, the semiconducting material according to claim 9.

11. The electronic device according to claim 10, which is an organic light emitting diode.

12. The electronic device according to claim 10, wherein the compound having formula (I) is comprised in a hole injecting layer and/or in a hole transporting layer and/or in a charge generating layer.

13. A semiconducting layer consisting of the semiconducting material according to claim 9.

14. A semiconducting layer consisting of the semiconducting material according to claim 7.

15. An electronic device comprising, between a first and a second electrode, the semiconducting layer according to claim 14.

16. The electronic device according to claim 15, which is an organic light emitting diode.

17. The electronic device according to claim 15, wherein the compound having formula (I) is comprised in a hole injecting layer and/or in a hole transporting layer and/or in a charge generating layer.

18. Use of the compound according to claim 7 as a p-dopant in a semiconducting material, in a semiconducting layer, or in an electronic device.

19. A process for synthesis of the [3]-radialene compound according to claim 7,
wherein a last synthesis step consists of oxidizing a reduced form of the compound of formula (I) to form the compound of formula (I), and the last synthesis step is carried out in a solvent comprising at least one saturated halogenated carboxylic acid.

* * * * *